(12) United States Patent
Wu et al.

(10) Patent No.: US 9,345,788 B2
(45) Date of Patent: *May 24, 2016

(54) RECONSTITUTED HUMAN BREAST TUMOR MODEL

(75) Inventors: Min Wu, Winchester, MA (US); Charlotte Kuperwasser, Boston, MA (US); Murray Robinson, Boston, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 1630 days.

This patent is subject to a terminal disclaimer.

(21) Appl. No.: 11/170,338

(22) Filed: Jun. 28, 2005

(65) Prior Publication Data
US 2006/0123494 A1  Jun. 8, 2006

Related U.S. Application Data

(63) Continuation-in-part of application No. 11/006,413, filed on Dec. 7, 2004, now abandoned.

(51) Int. Cl.
*A01K 67/027* (2006.01)
*A61K 49/00* (2006.01)

(52) U.S. Cl.
CPC .......... *A61K 49/0008* (2013.01); *A01K 67/0271* (2013.01); *A01K 2227/105* (2013.01); *A01K 2267/0331* (2013.01); *C12N 2510/04* (2013.01); *C12N 2799/027* (2013.01)

(58) Field of Classification Search
None
See application file for complete search history.

(56) References Cited

U.S. PATENT DOCUMENTS

| | | | |
|---|---|---|---|
| 6,261,836 | B1 | 7/2001 | Cech et al. |
| 6,639,121 | B1 | 10/2003 | DePinho et al. |
| 2005/0193432 | A1 | 9/2005 | Kuperwasser et al. |
| 2006/0161999 | A1 | 7/2006 | Wu et al. |

FOREIGN PATENT DOCUMENTS

| | | |
|---|---|---|
| WO | WO 02/079419 | 10/2002 |
| WO | WO 2005/049811 | 6/2005 |

OTHER PUBLICATIONS

Parmar et al., Endocrinology, 2002, 143: 4886-4896.*
Lohr et al., Virchow Arch, 2001, 438: 581-590.*
Omer et al., Cancer Res, 2000, 60: 2680-2688.*
Popnikolov et al., J Endocrinol, 2001, 168: 487-496.*
Fan et al., Oncogene, 1997, 14: 2595-2607.*
Tilli et al., Breast Cancer Research, 2003, 5: 202-205.*
Li et al., Oncogene, 1998, 16: 997-1007.*
Mamay et al., Cancer Lett., 2001, 168: 165-172.*
Heppner et al., Breast Cancer Res., 2000, 2: 331-334.*
Woods et al., Oncogene, 1994, 9: 2943-2950, Abstract.*
Chang et al., Virology, 1985, 146: 246-261.*
Jat et al., Mol. Cell Biol., 1986, 6: 1204-1217.*
Rhim et al., Oncogene, 1989, 4: 1403-1409, Abstract.*
Yuan et al., J Virol, 2002, 76: 10685-10691.*
Foddis et al., Oncogene, 2002, 21: 1434-1442.*
Mulligan et al., Science, 1980, 209: 1422-1427.*
Paucha et al., J. Virol., 1986, 57: 50-64.*
Brummelkamp, T.R. et al., "A System for Stable Expression of Short Interfering RNAs in Mammalian Cells," *Science* 296: 550-553 (2002).
DeOme, K.B. et al., "Development of Mammary Tumors from Hyperplastic Alveolar Nodules Transplanted into Gland-free Mammary Fat Pads of Female C3H Mice," *Cancer Res.* 19:515-520 (1959).
Edwards, P.A.W. et al., "Genetic Manipulation of Mammary Epithelium by Transplantation," *J. Mammary Gland Biol. Neoplasia* 1:75-89 (1996).
Edwards, P.A.W., "Tissue Reconstitution Models of Breast Cancer," in Cancer Surveys vol. 16: *The Molecular Pathology of Cancer*, N.R. Lemoine and N.A. Wright (Eds.), Cold Spring Harbor Laboratory Press, 79-96 (1993).
Elenbaas, B., et al., "Human breast cancer cells generated by oncogenic transformation of primary mammary epithelial cells," *Genes & Development* 15:50-65 (2001).
Fan, J., et al., "K-ras modulates the cell cycle via both positive and negative regulatory pathways," *Oncogene* 14:2595-2607 (1997).
Gudjonsson, T. et al., "Isolation, immortalization, and characterization of a human breast epithelial cell line with stem cell properties," *Genes & Development* 16:693-706 (2002).
Gupta P.B. et al., "Disease models of breast cancer," *Drug Discovery Today: Disease Models*, Elsevier, 1:9-16 (2004).
Hahn, W.C., et al., "Creation of human tumour cells with defined genetic elements," *Nature* 400:464-468 (1999).
Jensen, H.M. et al., "Preneoplastic Lesions of the Human Mammary Gland Transplanted into the Nude Athymic Mouse," *Cancer Res.* 36:2605-2610 (1976).
Kuperwasser et al., "Reconstruction of functionally normal and malignant human breast tissues in mice," *PNAS.* 101:4966-4971 (2004).
Kuperwasser, C. et al., "A mouse model of human breast cancer metastasis to human bone," *Cancer Res.*, 65:6130-6138 (2005).
Löhr, M. et al., "Immortalized bovine pancreatic duct cells become tumorigenic after transfection with mutant k-ras," *Virchow Arch.* 438:581-590 (2001).
Lundberg, A.S. et al., "Immortalization and transformation of primary human airway epithelial cells by gene transfer," *Oncogene* 21:4577-4586 (2002).
Maas-Szabowski, N. et al., "Organotypic Cocultures with Genetically Modified Mouse Fibroblasts as a Tool to Dissect Molecular Mechanisms Regulating Keratinocyte Growth and Differentiation," *J. Invest. Dermatol.* 116:816-820 (2001).

(Continued)

*Primary Examiner* — Ileana Popa
(74) *Attorney, Agent, or Firm* — Goodwin Procter LLP

(57) ABSTRACT

A reconstituted human breast tumor model is disclosed. The model, which is incorporated into mice, provides actual tumors that arise spontaneously, thereby mimicking naturally occurring breast cancer. The tumors are genetically human, because they arise from human mammary tissues that develop from human mammary epithelial cells implanted into host mice. Prior to implantation, the mammary epithelial cells are genetically modified to contain a recombinant human oncogene and an SV40 early region.

5 Claims, 2 Drawing Sheets

(56) References Cited

OTHER PUBLICATIONS

McManus, M.J. et al., "Hormone-induced Ductal DNA Synthesis of Human Breast Tissues Maintained in the Athymic Nude Mouse," *Cancer Res.* 41:3300-3305 (1981).

McManus, M.J. et al., "The Effect of Estrogen, Progesterone, Thyroxine, and Human Placental Lactogen on DNA Synthesis of Human Breast Ductal Epithelium Maintained in Athymic Nude Mice," *Cancer* 54:1920-1927 (1984).

Medina, D., "Stromal fibroblasts influence human mammary epithelial cell morphogensis." *Proc. Natl. Acad. Sci. USA*, 101:4723-4724 (2004).

Nakamura, H. et al., "Establishment of Immortal Normal and Ataxia Telangiectasia Fibroblast Cell Lines by Introduction of the hTERT Gene," *J. Radiat. Res.* 43:167-174 (2002).

Omer, A.C., et al., "Mouse mammary tumor virus-ki-rasB transgenic mice develop mammary carcinomas that can be growth-inhibited by a farnesyl:protein transferase inhibitor," *Cancer Res.* 60:2680-2688 (2000).

Outzen, H.C. et al., "Growth of Human Normal and Neoplastic Mammary Tissues in the Cleared Mammary Fat Pad of the Nude Mouse," *J. Natl. Cancer Inst.* 55:1461-1466 (1975).

Parmar, H. et al., "A Novel Method for Growing Human Breast Epithelium in Vivo Using Mouse and Human Mammary Fibroblasts," *Endocrinology* 143:4886-4896 (2002).

Parmar, H. et al., "Epithelial-stromal interactions in the mouse and human mammary gland in vivo," *Endocrine-Related Cancer* 11:437-458 (2004).

Popnikolov, N., et al., "Reconstituted normal human breast in nude mice: effect of host pregnancy environment and human chorionic gonadotropin on proliferation," *J. of Endocrinology* 168:487-496 (2001).

Southern, P.J. et al., "Transformation of Mammalian Cells to Antibiotic Resistance with a Bacterial Gene Under Control of the SV40 Early Region Promoter," *J. Mol. Appl. Genet.* 1:327-341 (1982).

Wu M. et al., "Genetically engineered human breast tumor in mice," *Breast Cancer Research and Treatment*, 94:S10 (Abstract) (2005).

Hahn et al., "Enumeration of the Simian Virus 40 Early Region Elements Necessary for Human Cell Transformation," *Mol. Cell. Biol.*, Apr. 2002, p. 2111-2123 (including Erratum published in *Mol. Cell. Biol.* May 2002; 22(10): 3562).

\* cited by examiner

RECONSTITUTED HUMAN BREAST TUMOR MODEL

RELATED APPLICATIONS

This application claims priority from U.S. application Ser. No. 11/006,413, filed Dec. 7, 2004.

FIELD OF THE INVENTION

The field of the invention is molecular biology and oncology.

BACKGROUND OF THE INVENTION

Conventional human-in-mouse xenograft models offer the advantage of working with human cancer cells in vivo. A disadvantage, however, is that the human cells have been maintained in culture as distinct cell lines (NCI 60 panel) for many years. This can lead to significant differences between the properties and behavior of the xenografted cells as compared to primary tumor cells. To address the need to work with primary tumor cells, in vivo models that provide spontaneous tumors in mice have been developed. See, e.g., U.S. Pat. No. 6,639,121. In these models, however, the tumor cells are mouse tumor cells. Therefore, for human cancer research, extrapolation of experimental results across species is still necessary.

SUMMARY OF THE INVENTION

A technique for producing genetically human breast tumors in mice has been discovered. Based on this discovery, the invention features a mouse that contains a reconstituted human breast tumor model. The model includes at least one spontaneous tumor. The tumor contains a plurality of human mammary epithelial cells, which contain a recombinant human oncogene and the recombinant SV40 early region. Preferably, the tumor growth site is a mammary fat pad of the mouse, a gonadal fat pad of the mouse, a kidney capsule of the mouse, or a subcutaneous site, e.g., on a flank of the mouse. In some embodiments of the invention, the model also includes a plurality of human fibroblast cells, e.g., human mammary fibroblast cells. Some or all of the human fibroblast cells can be located in the tumor. The human fibroblast cells can be carcinoma associated fibroblasts, or genetically engineered fibroblasts, e.g., immortalized fibroblasts, as well as primary human fibroblasts.

Examples of human oncogenes that can be introduced into the human mammary epithelial cells in according to the invention include K-RAS, H-RAS, N-RAS, EGFR, MDM2, RhoC, AKT1, AKT2, c-myc, n-myc, β-catenin, PDGF, C-MET, PI3K-CA, CDK4, cyclin B1, cyclin D1, estrogen receptor gene, progesterone receptor gene, ErbB1, ErbB2 (also called HER2), ErbB3, ErbB4, TGFα, TGF-β, ras-GAP, Shc, Nck, Src, Yes, Fyn, Wnt, and $Bcl_2$ PyV MT. Preferred human oncogenes are KRAS, ErbB2, and cyclin D1.

In some embodiments of the invention, the recombinant human oncogene is operably linked to an inducible promoter. Examples of useful inducible promoters include a tetracycline-inducible promoter, a metallothionine promoter, the IPTG/lacI promoter system, an ecdysone promoter system, and a mifepristone-inducible promoter. A preferred inducible promoter is the tetracycline inducible promoter.

The invention also provides a method of making a mouse that comprises a reconstituted human breast tumor model. The method includes the following steps: providing nontumorigenic human fibroblasts; providing human mammary epithelial cells; introducing into the human mammary epithelial cells a recombinant human oncogene and the recombinant SV40 early region; and implanting the nontumorigenic human fibroblasts and the transduced human mammary epithelial cells, in close proximity to each other, in a mouse. The fibroblasts and epithelial cells can be implanted at sites including, but not limited to, a mammary fat pad, a gonadal fat pad, a kidney capsule, or a subcutaneous site, e.g., a subcutaneous site on the flank of the mouse.

The invention also provides a method of identifying a cancer-related gene. The method includes the steps of: (a) providing tumor cells from a spontaneous tumor in a reconstituted human breast tumor model in a mouse, wherein the tumor contains a plurality of human mammary epithelial cells that contain (1) a recombinant human oncogene under the control of an inducible promoter, and (2) the SV40 early region; (b) introducing into the cells a nucleic acid that integrates into the genomes of the cells, thereby tagging the loci at which it integrates; (c) culturing the cells under conditions wherein no inducer for the inducible promoter is present; (d) identifying a cell in which tumorigenicity has been induced by integration of the nucleic acid molecule; and (e) identifying, as a cancer-related gene, a gene that has been tagged in the cell in step (c) by the integrated nucleic acid molecule. In some embodiments, the nucleic acid molecule includes a retroviral sequence, e.g., a Moloney murine leukemia virus.

The invention also provides a method of testing a compound for anti-tumor effects. The method includes the steps of: (a) providing a mouse that comprises a reconstituted human breast tumor model that includes a spontaneous tumor that contains a plurality of human mammary epithelial cells that contain a recombinant human oncogene and the recombinant SV40 early region; (b) administering the test compound to the mouse; and (c) detecting an anti-tumor effect, if any, of the test compound on the tumor, as compared to a suitable control.

The invention also provides a method of propagating a human breast primary tumor in a mouse. The method includes (a) providing human mammary epithelial cells from the tumor; (b) providing immortalized non-tumorigenic human mammary fibroblasts; (c) implanting the epithelial cells and the fibroblasts into a mouse, in close proximity to each other; and (d) maintaining the mouse for a time sufficient to propagate the tumor. The epithelial cells and the fibroblasts can be implanted into the mouse in a mammary fat pad, a gonadal fat pad, or a subcutaneous flank site. In preferred embodiments of the invention the epithelial cells and fibroblasts are implanted in a mammary fat pad. In some embodiments, the mammary fat pad has been injected previously with immortalized non-tumorigenic human mammary fibroblasts. In some embodiments, of the invention, the epithelial cells and the fibroblasts are mixed prior to implantation and then implanted as a mixture of cells.

Unless otherwise defined, all technical and scientific terms used herein have the same meaning as commonly understood by one of ordinary skill in the art to which the invention pertains. In case of conflict, the present specification, including definitions, will control. All publications, patents and other references mentioned herein are incorporated by reference in their entirety.

Although methods and materials similar or equivalent to those described herein can be used in the practice or testing of the invention, the preferred methods and materials are described below. The materials, methods and examples are illustrative only, and are not intended to be limiting. Other features and advantages of the invention will be apparent from the detailed description and from the claims.

DETAILED DESCRIPTION OF THE INVENTION

Figure 1:
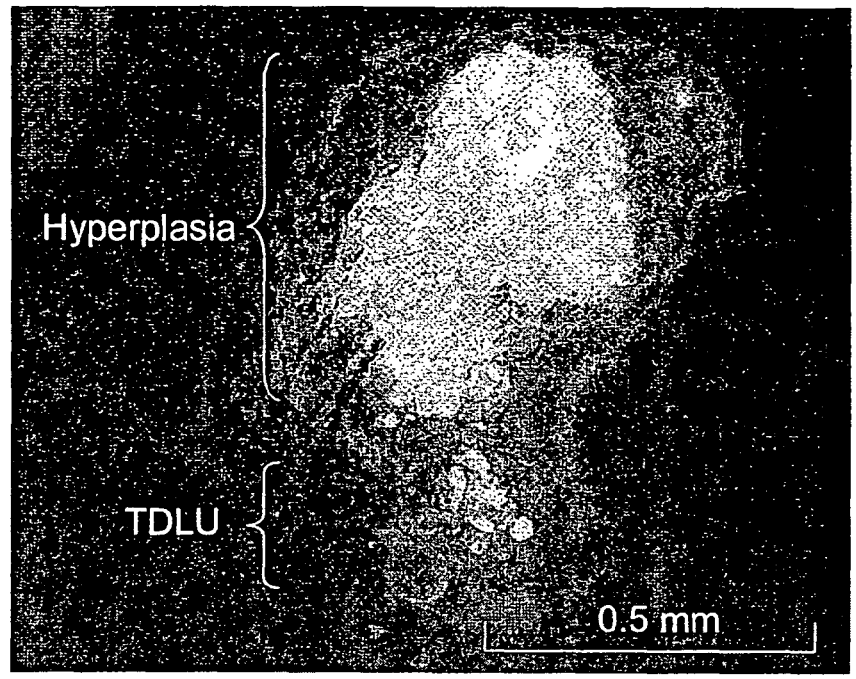
FIG. 1 is a photograph of a fluorescent whole mount of human breast tissue outgrowth from human mammary epithelial cells transduced with p53 RNAi, KRAS and green fluorescent protein (GFP). Human mammary epithelial cell organoids were infected with lentiviruses expressing p53 RNAi, KRAS and GFP. The mixture of infected and uninfected human mammary epithelial cells was injected into cleared fat pads which had previously been injected with immortalized human breast fibroblasts. Mammary glands were collected 6-months after implantation and subjected to UV microscopy. TDLU—terminal ductal lobular unit. The bracket indicates the area shown in FIG. 2.

The present invention provides a reconstituted human breast tumor model. In this model, tumors arise spontaneously from human mammary tissue growing in mice. For basic research on human cancer biology and for drug discovery and development, this model offers three major advantages. First, it provides primary tumors that arise spontaneously, thereby mimicking naturally occurring human breast cancer. Second, the tumors are genetically human, because they arise from human mammary glands that develop from human mammary epithelial cells implanted into host mice. Third, the tumors are generated by defined genetic elements, thereby providing opportunities to study pathway-related tumorigenesis in human primary tumors.

There is published evidence that mammary stromal fibroblast cells support the growth and differentiation of mammary epithelial cells. See, e.g., Parmar et al., 2002, *Endocrinology* 143:4886-4896; and Parmar et al., 2004, *Endocrine-Related Cancer* 11:437-458. Therefore, human fibroblasts, e.g., human mammary fibroblasts, can be used for this purpose in practicing the present invention. The human fibroblasts and human mammary epithelial cells are implanted in proximity to one another, e.g., within a single mammary fat pad, gonadal fat pad, or subcutaneous injection site. The human fibroblasts and human mammary epithelial cells can be mixed and co-injected at the selected site of implantation in the mouse. Optionally, the fibroblasts can be injected before injection of the epithelial cells, e.g., one to four weeks, to allow time for the fibroblasts to proliferate and invade the mouse tissue before introduction of the human mammary epithelial cells.

Mouse mammary epithelium develops postnatally by extending from the nipple area. By three weeks of age, the mammary ducts composed of mammary epithelial cells have not reached the lymph node. Therefore the mouse epithelial component of the mammary gland can be eliminated by removing the portion between nipple and the lymph nod, thereby leaving a "cleared" fat pad. See, e.g., De Ome et al., 1959, *Cancer Res.* 19:515-520; Edwards et al., 1996, *J. Mammary Gland Biol. Neoplasia* 1:75-89. In some embodiments of the invention, the human fibroblasts and human mammary epithelial cells are implanted into a cleared mammary fat pad of the host mouse. However, it is not necessary for the fat pad to be cleared.

In some embodiments of the invention, the fibroblasts and epithelial cells are implanted into a gonadal fat pad of the mouse. In other embodiments, the fibroblasts and epithelial cells are implanted into a kidney capsule of the mouse. See, e.g., Parmar et al., 2002, supra. Another alternative is to implant the fibroblasts and epithelial cells into the mouse subcutaneously, e.g., on a flank of the mouse.

Various relevant surgical techniques for implantation of the fibroblasts and epithelial cells into the mouse have been developed and are known in the art. See, e.g., Outzen et al., 1975, *J. Natl. Cancer Inst.* 55:1461-1466; Jensen et al., 1976, *Cancer Res.* 36:2605-2610; McManus et al., 1981, *Cancer Res.* 41:3300-3305; McManus et al., 1984, *Cancer* 54:1920-1927; Edwards, et al., supra. Typically, implantation is by injection, using a Hamilton syringe, but any suitable technique for introducing the human cells into the mouse can be employed.

Nontumorigenic human fibroblasts are human fibroblasts that do not form tumors on nude mice and do not form colonies in soft agar assays. The type of nontumorigenic human fibroblasts implanted generally is not critical. For convenience, immortalized fibroblasts can be used. Immortalized human fibroblasts are human fibroblasts that can divide indefinitely in vitro without entering senescence. Primary human stromal fibroblasts can be immortalized by any suitable method. Various methods are known in the art. For example, fibroblasts can be immortalized by stable transformation with an expression vector encoding human telomerase reverse transcriptase (hTERT). See, e.g., Cech et al., U.S. Pat. No. 6,261,836; see also, Nakamura et al., 2002, *J. Radiat. Res.* 43:167-174. Alternatively, primary fibroblasts, which normally are capable of surviving several passages in cell culture, can be used for implantation, in practicing the present invention. Another alternative is to use carcinoma associated fibroblasts (CAF). CAF cells can be isolated from human breast tumors, e.g., from mastectomy specimens.

A suitable source for isolation of human mammary fibroblasts for culture (and subsequent use in a fibroblast immortalization protocol or use as primary fibroblasts) is reduction mammoplasty tissue. The human tissue can be place into culture essentially as described by Parmar et al., 2002, *Endocrinology* 143: 4886-4896. The human fibroblast material can be expanded as necessary through conventional cell culture techniques.

Preferably, the mice used in the practice of the present invention are immunocompromised. A compromised immune system is desirable to prevent the mouse from rejecting the implanted human cells. Examples of immunocompromised mice include SCID mice, nude mice, mice whose thymus gland has been surgically removed, and mice whose immune system has been suppressed by drugs or genetic manipulations. Genetically immunocompromised mice are commercially available, and selection of immunocompromised mice suitable for purposes of the present invention is within ordinary skill in the art.

In practicing the present invention, nucleic acids can be introduced into the nontumorigenic human fibroblasts and human mammary epithelial cells by any method that leads to stable transformation. Examples of useful transformation methods known in the art include spheroplast fusion, liposome fusion, calcium phosphate precipitation, electroporation, microinjection, and infection by viral vectors such as retroviruses, adenoviruses, and lentiviruses. Suitable eukaryotic expression vectors are known in the art and are commercially available. Typically, such vectors contain convenient restriction sites for insertion of the desired recombinant sequences. The vectors can include a selectable marker, e.g., a drug resistance gene. An exemplary drug resistance gene is the neomycin phosphotransferase (neo) gene (Southern et al., 1982, *J. Mol. Anal. Genet.* 1:327-341), which confers neomycin resistance. Alternatively, genes encoding fluorescence markers, e.g., green fluorescent protein, yellow fluorescent protein or blue fluorescent protein; or genes encoding bioluminescent proteins, e.g., luciferase, can be used as selectable markers.

In some embodiments of the invention, the recombinant oncogene is placed under the control of an inducible promoter. Examples of inducible promoters useful for this purpose include a tetracycline-inducible promoter, a metallothionine promoter, the IPTG/lacI promoter system, and the ecdysone promoter system. In addition, the "lox stop lox" system can be used for irreversibly deleting inhibitory sequences for translation or transcription. An inducible oncogene construct can be used in making genetically modified human mammary epithelial cells according to the invention, which are implanted in a host mouse according to the invention. The implanted human mammary epithelial cells are maintained in the presence of the inducer, e.g., by administering the inducer in the drinking water of the host mouse, until a tumor forms. Then tumor cells are explanted and cultured in the absence of the inducer. At this point, the explanted tumor cells are only "one hit," i.e., one mutation, away from being tumorigenic.

A nucleic acid molecule, e.g., a retroviral vector, that integrates into the genomes of these cells can provide the necessary mutation to trigger tumorigenesis. If the vector is designed to tag the site where it integrates, it can be used to identify those genes whose activation (or inactivation) leads to tumorigenesis. Explanted tumor cells can be analyzed for tumorigenicity in the absence of the inducer, for example, by re-implantation into an animal such as a nude mouse, and monitoring for tumor formation. If an implanted cell gives rise to a tumor, the vector insertion site is cloned and sequenced, and the surrounding genes are mapped and identified. In this way, genes that functionally complement the recombinant oncogene are identified. Such genetic complementation is useful for identifying targets for oncology therapeutics. This approach for identifying cancer-related genes has been described in detail and is known as a "MaSS" screen. The MaSS screen technique can be incorporated readily into the methods of the present invention, which utilize the human reconstituted breast tumor model. For a detailed description of the MaSS screen, see PCT International patent publication WO 02/079419.

As described above, this invention provides an inducible human breast cancer model useful to study tumor biology and to screen for anti-cancer drugs. In some embodiments, the reconstituted breast tumor model provides human breast tissues whose genome has been modified to include: (a) an oncogene, e.g., a ErbB2 gene or KRAS gene, operably linked to an inducible promoter, and (b) the SV40 early region, that together cause the human breast tissue to have a greater susceptibility to cancer than reconstituted human breast tissue not containing these genetic modifications. The tumor regresses when expression of the oncogene is turned off. Optional mutations that would render the reconstituted human breast tissue even more susceptible to cancer include disabling mutations in a DNA repair gene (e.g., MSH2), and activating mutations in an oncogene (e.g., myc and ras).

In one embodiment, the reconstituted human breast tissue develops from injected human mammary epithelial cells comprising (i) a first expression construct containing a gene encoding a reverse tetracycline transactivator operably linked to a suitable promoter, and (ii) a second expression construct containing the oncogene operably linked to a promoter regulated by the reverse tetracycline transactivator and tetracycline (or a tetracycline analogue, e.g., doxycycline). The host mouse is observed with and without administration of tetracycline (or analogue thereof) for the development, maintenance, or progression of a tumor that is tetracycline-dependent. Other inducible systems such as those described above also can be employed. When doxycycline is used as an inducer for a reverse tetracycline transactivator-controlled inducible promoter system, a preferred method for administering doxycycline is administration through the animals' drinking water.

The ability to compare the effect of a test compound to the effect of genetically switching off the inducible oncogene in this system allows the identification of surrogate markers that are predictive of the clinical response to the compound. The inducible model can be used to determine whether a compound can eradicate minimal residual tumor. Normally in the inducible model, a tumor regresses when the oncogene is switched from "on" to "off" using the inducible promoter. But if a test compound can eradicate minimal residual tumor, switching the gene back on after administration of the test compound will not bring back the tumor.

Reconstituted breast tumor models according to the invention are useful in methods of determining the efficacy of a test compound in preventing or treating cancer. Such methods involve administering test compounds to host mice and observing the effect(s), if any, of the compounds on tumor development, tumor maintenance, tumor progression or angiogenesis in the mice. Regression and/or reduction of tumor size in the presence of the compound, as compared to an appropriate control, indicates an anti-tumor effect of the compound. This type of drug efficacy testing can be performed using a model in which the oncogene is inducible or noninducible.

The model also can be used to identify other cancer-related genes. To do this, a detailed expression profile of gene expression in tumors undergoing regression or regrowth due to the inactivation or activation of the oncogene is established. Techniques used to establish the profile include the use of suppression subtraction (in cell culture), differential display, proteomic analysis, serial analysis of gene expression (SAGE), and expression/transcription profiling using cDNA and/or oligonucleotide microarrays. Then, comparisons of expression profiles at different stages of cancer development can be performed to identify genes whose expression patterns are altered.

As used herein, "test compound" means macromolecules, e.g., polypeptides, nucleic acids, polysaccharides and lipids, as well as small molecules. Test compounds can be administered to host mice comprising reconstituted human breast tumor models of this invention through oral, rectal, vaginal, topical nasal, ophthalmic or parenteral administration. Parenteral administration includes subcutaneous, intravenous, intramuscular, and intrasternal injection, and infusion techniques. An exemplary route of administration for mouse experimentation is injection into the tail vein.

Preferably, test compounds are formulated in a manner that takes into account factors such as the dosage, compound solubility and route of administration. Solid formulations for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, e.g., microcrystalline cellulose, corn starch, sodium starch glycolate, and alginic acid. Tablet binders include acacia, methylcellulose, sodium carboxymethylcellulose, polyvinylpyrrolidone (Povidone™), hydroxypropyl methylcellulose, sucrose, starch, and ethylcellulose. Examples of lubricants include magnesium stearates, stearic acid, silicone fluid, talc, waxes, oils, and colloidal silica. Liquid formulations for oral administration prepared in water or other aqueous vehicles can contain suspending agents such as methylcellulose, alginates, tragacanth, pectin, kelgin, carrageenan, acacia, polyvinylpyrrolidone, and polyvinyl alcohol. The liquid formulations also can include solutions, emulsions, syrups and elixirs containing, together with the active compound(s), wetting agents, sweeteners, and flavoring agents. Injectable formulations can contain carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). Physiologically acceptable excipients include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid (e.g., ethyl oleate). A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens. Pharmaceutical formulation is a well-established art, and is further described in Gennaro (ed.), Remington: *The Science and Practice of Pharmacy,* 20th ed., Lippincott, Williams & Wilkins (2000) (ISBN: 0683306472); Ansel et al., *Pharmaceutical Dosage Forms and Drug Delivery Systems,* 7th ed., Lippincott Williams & Wilkins Publishers (1999) (ISBN: 0683305727); and Kibbe (ed.), *Handbook of Pharmaceutical Excipients* American Pharmaceutical Association, 3rd ed. (2000) (ISBN: 091733096X).

Numerous parameters can be employed to determine whether a test compound displays "an anti-tumor effect." Examples of such parameters include amount of apoptosis in the tumor tissue, level of angiogenesis in the tumor tissue, number of hyperplastic growths such as ductal hyperplasias, effects on differentiation or morphogenesis of the tumor tissue, or simply the size, e.g., diameter or volume of the tumor. The choice of parameter(s) to be measured, and their interpretation, will depend on the objectives of the particular experiment. Such choice and interpretation is within ordinary skill in the art.

There is considerable latitude in experimental design. For example, in one type of experimental design, test animals and control animals may be separate and substantially identical. In another type of experimental design, test compound and vehicle may be administered locally to separate tumors, e.g., left side and right side, on the same animal. Of course, a panel of animals can receive a range of dosages in dose-response studies.

EXAMPLES

The invention is further illustrated by the following examples. The examples are provided for illustrative purposes only, and are not to be construed as limiting the scope or content of the invention in any way.

Example 1

Construction of Breast Tumor Model

Human Tissues and Cell Lines

Fresh human breast tissue from reduction mammoplasty surgical procedures was obtained from Dr. Andrea Richardson at the Brigham and Women's Hospital, Boston, Mass., in compliance with institutional guidelines and with IRB approval. The fresh tissue was digested overnight at 37° C. using 2.8 mg/ml collagenase and 0.6 mg/ml Hyaluronidase in HMEC medium (F12 medium containing 5% fetal bovine serum, 10 ug/ml insulin, 10 ng/ml EGF, 10 µg/ml Hydrocortisone, 50 U/ml penicillin, 50 ug/ml streptomycin and 0.25 µg/ml Fungizone). The following morning, the digested human breast tissue, consisting of epithelial organoids (clusters of about 10 to 1,000 epithelial cells) and primary fibroblasts, was collected by centrifugation at 1000 rpm for 5 minutes and then washed three times in PBS+5% FBS. The mixture of epithelial organoids and primary fibroblasts were frozen in freezing medium (10% DMSO, 15% fetal bovine serum, 10 µg/ml insulin, 10 ng/ml EGF, 10 µg/ml Hydrocortisone, 50 U/ml penicillin, 50 µg/ml streptomycin and 0.25 µg/ml Fungizone) and stored in liquid nitrogen.

The immortalized human mammary fibroblast cell lines were provided by Charlotte Kuperwasser at the Whitehead Instituted.

Vector Constructs

Lentivirus vectors were used for transduction of the human mammary epithelial cells. The lentivirus backbone used in constructing all of the following lentivirus vectors was pLenti6/V5-D-TOPO, which is commercially available from Invitrogen (Carlsbad, Calif.; cat. # K4955-10).

The vector pLenti-CMV-SV40 early was constructed as follows. A 2.7 kb SV40 early region DNA fragment (including LT and st) was obtained by digesting the pSV3-dhfr vector (ATCC #37147) with Sfi I and BamH I. The 2.7 kb fragment was then cloned behind the CMV promoter in vector pLenti6/V5-D-TOPO. SV40-Blastocidin DNA fragment was then removed from the resulting construct to generate the pLenti-CMV-SV40 early lentivirus construct.

The vector pLenti-CMV-KRAS was constructed as follows. Similar to the pLenti-CMV-SV40 early construct, a 558 bp KRAS cDNA fragment was cloned behind the CMV promoter in vector pLenti6/V5-D-TOPO. The KRAS used in making this construct was the $KRAS^{G12V}$. The Genbank accession number for wild-type KRAS cDNA is NM_033360. We used KRAS$^{G12V}$ (a gift from Linda Chin, Harvard University Medical School), a mutant form in which amino acid residue 12 is changed from glycine to valine.

The vector pLenti-CMV-ErbB2 was constructed as follows. A 3992 bp ErbB2 cDNA fragment was cloned behind the CMV promoter in vector pLenti6/V5-D-TOPO (Invitrogen; cat. # K4955-10). The ErbB2 used in making this construct was the ErbB2$^{V659E}$. The accession number for wild-type ErbB2 cDNA is M11730. Site directed mutagenesis was employed to change amino acid residue 659 from V to E.

The vector pLenti-U6-p53RNAi-CMV-ErbB2 was constructed as follows. The p53 RNAi sequence was as described in Brummelkamp et al., 2002, Science 296:550-553. The U6-p53RNAi cassette was placed before CMV promoter in pLenti-CMV-ErbB2 to generate this vector.

The vector pLenti-U6-p53RNAi-CMV-KRAS was constructed as follows. The p53RNAi sequence was as described in Brummelkamp et al., 2002, Science 296:550-553. The U6-p53RNAi cassette was placed before CMV promoter in pLenti-CMV-KRAS to generate this vector.

Lentiviruses were produced by cotransfection of 293T cells with the lentivirus constructs described above and the optimized packaging plasmid mix (Invitrogen; catalog no. K4975-00). Transfections were carried using the Lipofectamine™ 2000 Transfection Reagent according to the vendor's instructions (Invitrogen; catalog #11668-019).

Clearing Fat Pads and Injecting Fibroblasts

Immortalized human fibroblasts were then injected into the cleared fat pads either immediately after clearing of the fat pad or approximately two weeks after the fat pads were cleared. Prior to injection, the immortalized human fibroblasts were cultured in DMEM medium containing 10% FBS, 50 U/ml penicillin and 50 µg/ml streptomycin. Half of the fibroblasts used in for injection into cleared fat pads were treated with 2 mU/ml bleomycin for 30 minutes on the day before injection. On the day of injection, 1:1 mix of bleomycin treated fibroblasts and untreated fibroblasts are injected into the cleared fat pads at $0.5 \times 10^6$ cells/injection site.

Transducing Human Mammary Epithelial Cells

The mixture of human epithelial organoids and primary fibroblasts were cultured in DMEM medium containing 10% FBS for 4 hours, during which time the fibroblasts attached to the culture dish. The unattached organoids were collected from the supernatant and subject to two rounds of spin infection. During the first round of spin infection, about 50 µl of organoid pellet were resuspended in 1 ml HMEC medium containing $10^6$ to $10^9$ cfu lentivirus expressing the SV40 early region (prepared from lentivirus construct pLenti-CMV-SV40 early). The organoid/virus mixture was plated into one well of a 6-well culture plate, and spun for 90 minutes at 1500 rpm. At the end of the infection, 1 ml of fresh HMEC medium was added to the well. The plate was put back to 37° C. incubator overnight. On the following morning, the organoids were still not attached to the plate and were collected from the supernatant and subjected to a second round of spin infection. Similar to the first infection, organoid pellet were resuspended in 1 ml HMEC medium containing $10^6$ to $10^9$ cfu lentivirus expressing either KRAS or ErbB2 oncogene (prepared from lentivirus construct pLenti-CMV-KRAS or pLenti-CMV-ErbB2 separately). At the end of the second spin infection, 1 ml of fresh HMEC medium were added to the organoid suspension which were put back into the incubator. The infected organoids were then ready for injection into fat pads.

Injection of Infected Organoids

About 1 to 100 infected organoids were: (a) injected alone into a fat pad that had been injected with human fibroblasts two weeks previously; or (b) injected after mixing with $0.25 \times 10^6$ carcinoma associated fibroblasts (CAF), or (c) injected after mixing with a mixture of $0.25 \times 10^6$ bleomycin-treated immortalized human fibroblasts and $0.25 \times 10^6$ non-treated immortalized human fibroblasts. The cell preparation were resuspend in 1:1 mix of collagen:matrigel mix and injected in volume of about 30 to 50 µl per injection site.

Example 2

Efficiency of Lentivirus Infection and RNAi

To determine the efficiency of lentivirus infection of human mammary epithelial cells, a lentivirus construct was generated in which KRAS was placed behind the CMV promoter and EYFP (enhanced green fluorescent protein) was placed behind the SV40 promoter (pLenti-CMV-KRAS+SV40-EYFP). Human mammary epithelial cell organoids were infected with lentivirus expressing pLenti-CMV-KRAS+SV40-EYFP. The organoids were cultured for 3 more days after infection. Judging by the percentage of green fluorescent cells when observed under UV light, we concluded that about 50% of the human mammary epithelial cells were infected with pLenti-CMV-KRAS+SV40-EYFP lentivirus. Similarly, about 10% of the human mammary epithelial cells were infected with pLenti-CMV-ErbB2+SV40-EYFP lentivirus in a separate experiment. Therefore, depending on the titer of the virus used, about 10% to about 50% of the human mammary epithelial cells were infected with lentiviruses.

To determine the efficiency of p53RNAi in knocking down the expression of p53 and to determine the efficiency of gene transfer through lentivirus, 293T cells and HMEC organoids were infected with lentivirus expressing pLenti-U6-p53RNAi+CMV-KRAS+SV40-EYFP. Three days after infection, the cells were observed under UV light for estimation of infection rate and were collected for analyzing p53 and KRAS expression by real-time RT-PCR. Almost all of 293T cells were infected with the lentivirus. Since the expression level of p53 in infected 293T cells was about 3.6% of mock infected cells, we concluded that about 97.4% knockdown of p53 transcription was achieved in 293T cells through lentivirus infection. For the well of human mammary epithelial cells, about 50% of the cells were infected with the lentivirus. And since the expression level of p53 in those mixture of infected and non-infected human mammary epithelial cells is about 50% of the mock-infected human mammary epithelial cells, we concluded that close to 100% knockdown of p53 transcription was also achieved in human mammary epithelial cells through lentivirus infection. Similarly, KRAS expression was increased by close to 70-fold in both 293T cells and in human mammary epithelial cells by lentivirus infection.

Example 3

Transduction with p53 RNAi and ErbB2 or KRAS

Human mammary epithelial cells transduced with p53 RNAi and ErbB2 or KRAS developed hyperplasia in the reconstituted human in mouse mammary gland. As a first step towards generating human breast tumor model in mouse, we transduced human mammary epithelial cells with p53RNAi plus either ErbB2$^{V659E}$ or KRAS$^{G12V}$, through lentivirus transduction. The infected human mammary epithelial cells were either mixed with human breast fibroblasts prior to injection or injected alone into fat pads that had been injected with immortalized human fibroblasts two weeks previously.

Figure 2:
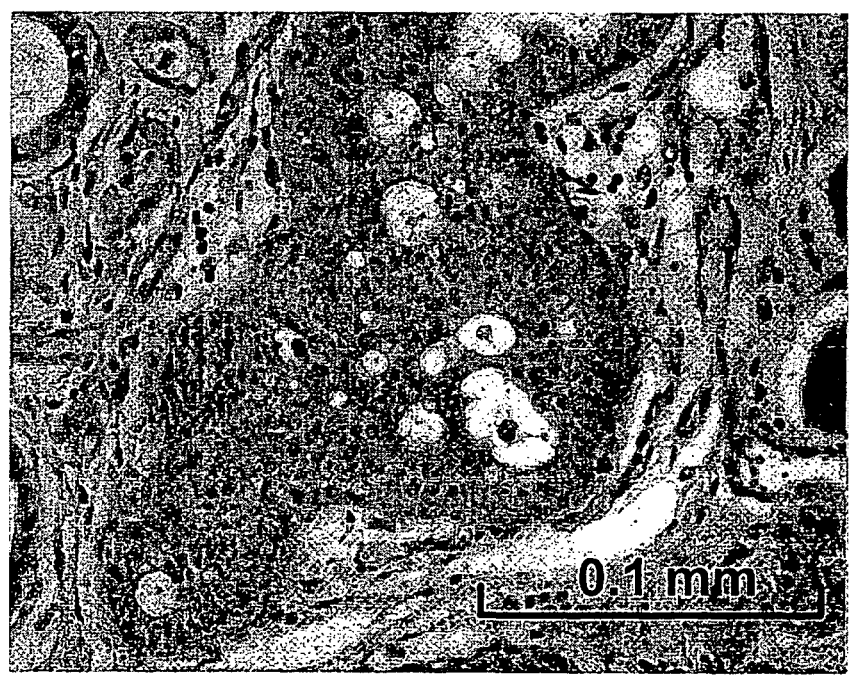
FIG. 2 is a hematoxylin and eosin-stained section from the intensely fluorescent area of the mammary gland image in FIG. 1 (magnification: 40×). Hyperplasia is developed from the human mammary epithelial cells transduced with p53 RNAi, KRAS and GFP.

In all combinations, normal, e.g. terminal ductual lobular unit, and hyperplastic human breast structures developed at the implantation sites between one to twelve month after implantation (FIGS. 1 and 2). However, no tumor developed from the transduced human mammary epithelial cells.

Example 4

Transduction with SV40 Early Region and ErbB2 or KRAS

Human mammary epithelial cells transduced with the SV40 early region and ErbB2 or KRAS developed human mammary tumors in the reconstituted mammary gland. We next transduced human mammary epithelial cells with SV40 early region plus ErbB2 or KRAS through lentivirus. The transduced human mammary epithelial cells were either mixed with immortalized human fibroblasts prior to injection or injected alone into fat pads that had been previously injected with immortalized human fibroblasts. In all combinations, tumors developed from the infected human mammary epithelial cells with tumor latency ranging from one to three months. More tumors developed from human mammary epithelial cells plus immortalized human fibroblasts than from human mammary epithelial cells alone. This indicated that the stroma affects tumorigenesis.

Figure 3:
FIG. 3 is a photograph of primary human breast tumors developed from human mammary epithelial cells transduced with SV40 early region and KRAS. Human mammary epithelial cell organoids were infected with lentiviruses expressing SV40 early region and KRAS. The mixture of infected and uninfected human mammary epithelial cells was injected into cleared fat pads which had previously been injected with immortalized human breast fibroblasts. Mammary glands were collected one month after implantation. It can be seen in this image that the tumor was well vascularized.
Figure 4:
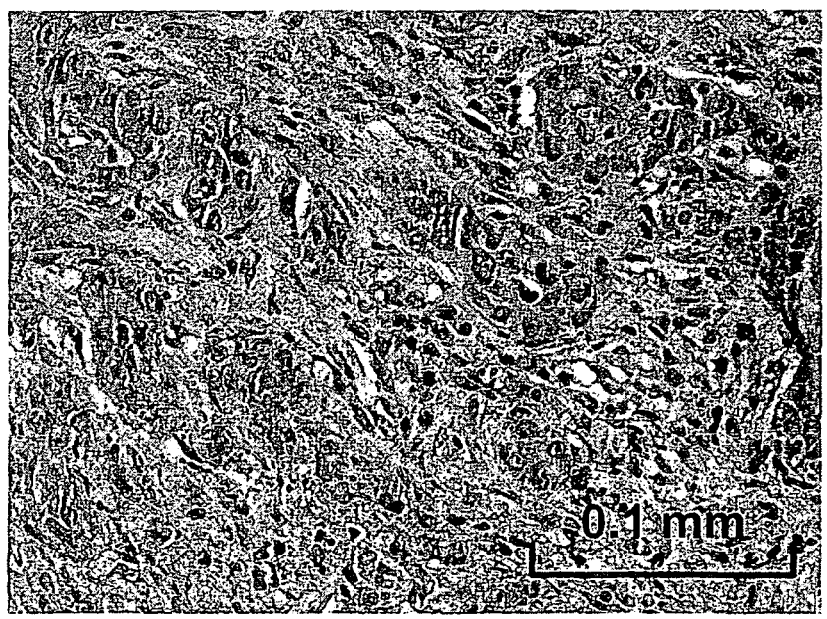
FIG. 4 is a hematoxylin and eosin-stained section from the human breast tumor shown in FIG. 3. The tumor developed is a poorly differentiated invasive adenocarcinoma. The high stromal component, invading nests and islands of tumor cells, and the high levels of cellular pleomorphism are characteristics of human breast cancer.

Two independent pathologists, Dr. Andrea Richardson at Brigham & Women's hospital and Dr. Marcus Bosengburg at Vermont University, examined the H&E staining of the tumor sections and concluded that the tumors developed were poorly differentiated invasive adenocarcinomas (FIGS. 3 and 4). The tumors that developed display no marked differences from human tumors. They looked much more like human breast (ductal) adenocarcinoma than most tumors arising in mouse breast. This was because of the higher stromal component, the architecture of the invading nests and islands of tumor cells, and the high levels of cellular pleomorphism.

Example 5

MaSS Screen

This example describes a procedure for identifying cancer-related genes in human cells.

Retroviral Infection of Tumor Cells

Mo-MuLV producer cell line TMJ (NIH3T3 based cell line) is plated to the required number of plates (100 mm). These cells are cultured and maintained in RPMI media with 10% FBS. For viral production, TMJ cells are fed with 4-5 ml of fresh culture media, and culture supernatant is harvested 8-12 hours later. The supernatant is filtered through a 0.45 μM filter.

Since human cells do not express the ecotropic receptor, they cannot be infected by Mo-MuLV. The human breast cancer cells are first transduced by MCAT1, the ecotropic receptor gene, through infection of lentiviruses expressing MCAT1 plus the blastocydin selection marker. The blastocydin resistant pseudotyped human breast cancer cells are then maintained in DMEM media with 10% fetal calf serum in the presence of doxycycline (2 μg/ml). At approximately 18-24 hours after plating, or when the plates are 70-80% confluent, the breast cancer cells are infected with the filtered viral supernatant in the presence of polybrene (6-8 μg/ml). From this point on, the breast cancer cells are maintained in the absence of doxycycline.

Approximately eighteen hours after infection, infected breast cancer cells are trypsinized, rinsed and resuspended in Hanks' Balanced Salt Solution. Cell suspensions are kept on ice, and the handling time after trypsinization is kept to a minimum. About $1 \times 10^6$ cells are injected onto the flank of SCID mice fed with water without doxycycline. The animals are observed for tumor development. Control animals are similarly injected with $1 \times 10^6$ uninfected cells. Tumors typically develop after approximately 21 days. Tumors are harvested and tumor tissues are immediately snap-frozen in liquid nitrogen.

Inverted Polymerase Chain Reaction

DNA is isolated from tumor tissues using the PUREGENE DNA isolation kit. Ten μg of genomic DNA is digested to completion with either BamHI or SacII and the reaction is terminated by incubation at 65° C. for 20 minutes. The digested samples are self-ligated in a diluted 600 μl reaction volume using 4000 U of high concentration T4 Ligase (NEB, Cat. # M0202M). The ligation is performed overnight to 24 hours at 16° C. The ligated DNA is precipitated with ethanol and dissolved in 40 μl of sterile water. The ligated DNA is then serially diluted to 1:10 and 1:100 ratios and subjected to inverted polymerase chain reaction (IPCR).

Identification of Candidate Genes

The site of retroviral integration into the human genome is mapped for all IPCR sequences as follows. Retroviral leader sequences are trimmed from the raw sequences of IPCR products, and homology searches for the trimmed sequences are performed in the NCBI MGSCV3 database by using the BLAST software program. BLAST hits are analyzed and recurrent sites of integration in multiple mouse tumors are identified. Recurrence are defined as two or more integrations within a 10 kb region. To identify genes whose expression is affected by the retroviral integration, NCBI Map View is used to identify the site of each recurrent retroviral integration onto the mouse genome. Genes immediately neighboring the site are identified by using the MGSCV3 Gene map. These genes are defined as candidate cancer-related genes because in the vast majority of cases; MuLV integration affects the most proximal genes. When the integration occurs within a gene, that gene is deemed the best candidate as the target for the effects of retroviral integration.

Example 6

Propagation of Human Breast Tumors in Mice

It has been difficult and impractical to propagate human primary breast tumors in mice (Sebesteny et al., 1979, *J. Natl. Cancer Inst.* 63:1331-7; Rae-Venter et al., 1980, *Cancer Res.*, 40:95-100; Sakakibara et al., 1996, *Cancer J. Sci. Am.* 2:291). Most tumors have grown very slowly in mice, with latencies of 6-12 months, or have failed to grow at all. Therefore, we decided to test the effect of phenotypic differences in surrounding primary human fibroblasts on the tumorigenicity of HUman Mammary Epithelial Cells (HUMECs) transfected with HER2 and the SV40 early region.

HUMECs and human fibroblasts were obtained and cultured as described in Example 1 (above). We implanted the HMECs, either alone or mixed with cultured human fibroblasts (RMF; Reduction Mammary Fibroblasts), into mouse mammary fat pads that had been previously injected with immortalized human fibroblasts expressing recombinant hepatocyte growth factor (HGF). The results are summarized in Table 1.

HMECs from five patients (HMEC5-HMEC9) consistently produced tumors (83% to 100% frequency) when transduced with the HER2/SV40 early region, and mixed with RMF-HGF (Reduction Mammoplasty Fibroblasts- Hepatocyte Growth Factor), at the time of implantation. In contrast, tumors developed rarely (0% to 17% (1/6)) when the same HMECs were transduced with the same genes (HER2 and SV40 early region), but mixed with primary human fibroblasts that were not immortalized (primary RMF 11 and primary RMF 13). When implanted without being mixed with any fibroblasts, the HER2/SV40 early region-transduced HMECs produced a tumor in 11% (1/9) of the implantation sites. Tumor latency ranged from one to three months. These results indicated that immortalized human fibroblasts promoted the tumorigenicity of HER2/SV40 early region transduced HMECs, whereas non-immortalized human primary mammary fibroblasts did not promote tumorigenicity, and perhaps inhibited it.

These data demonstrating the effect of human stromal fibroblasts on the rate of tumor development from HER2/SV40 early region-transduced HMECs indicate that, given the appropriate microenvironment by mixing with immortalized human fibroblasts, primary breast tumors from human patients will grow in mice, and thus, can be propagated efficiently in mice.

TABLE 1

Effect of stromal fibroblast phenotype on tumor formation by HER2/SV40 early-transduced HMECs in nude mice

| HMEC | Fibroblast | Tumor Frequency |
|---|---|---|
| HMEC5 | RMF-HGF[1] | 100% (14/14) |
| HMEC6 | RMF-HGF | 100% (6/6) |
| HMEC7 | RMF-HGF | 83% (5/6) |
| HMEC8 | RMF-HGF | 83% (5/6) |
| HMEC9 | RMF-HGF | 100% (6/6) |
| HMEC5 | RMF-GFP[2] | 75% (3/4) |
| HMEC5 | primary RMF[3] 11 | 0% (0/6) |
| HMEC5 | primary RMF 13 | 17% (1/6) |
| HMEC5 | no fibroblasts mixed with HMEC | 11% (1/9) |

[1]Immortalized RMF expressing HGF
[2]RMF expressing GFP reporter gene, but not recombinant HGF
[3]RMF not genetically engineered Other embodiments are within the following claims.

What is claimed is:

1. A mouse comprising a reconstituted human breast tumor model, wherein the model comprises a spontaneous tumor in a reconstituted human mammary gland, wherein the tumor comprises (a) a plurality of human primary mammary epithelial cells genetically modified with genetic modifications consisting of (i) a recombinant human oncogene and (ii) a recombinant SV40 early region, and (b) a plurality of nontumorigenic immortalized human mammary fibroblast cells.

2. The mouse of claim 1, wherein the recombinant oncogene is selected from the group consisting of K-RAS, H-RAS, N-RAS, EGFR, MDM2, RhoC, AKT1, AKT2, c-myc, n-myc, β-catenin, PDGF, C-MET, PI3K-CA, CDK4, cyclin B1, cyclin D1, estrogen receptor gene, progesterone receptor gene, ErbB1, ErbB2, ErbB3, ErbB4, TGF-α, TGF-β, ras-GAP, Shc, Nck, Src, Yes, Fyn, Wnt, and Bcl2.

3. The mouse of claim 2, wherein the recombinant human oncogene is selected from the group consisting of KRAS, ErbB2, and cyclin D1.

4. The mouse of claim 3, wherein the recombinant human oncogene is KRAS.

5. The mouse of claim 4, wherein the KRAS is KRASG12V.

* * * * *